US008133258B2

(12) United States Patent
Foerster et al.

(10) Patent No.: US 8,133,258 B2
(45) Date of Patent: Mar. 13, 2012

(54) METHOD AND APPARATUS FOR ATTACHING CONNECTIVE TISSUES TO BONE USING A KNOTLESS SUTURE ANCHORING DEVICE

(75) Inventors: Seth Foerster, San Clemente, CA (US); Francis Vijay, Irvine, CA (US); Norman Gordon, Irvine, CA (US)

(73) Assignee: ArthroCare Corporation, Austin, TX (US)

( * ) Notice: Subject to any disclaimer, the term of this patent is extended or adjusted under 35 U.S.C. 154(b) by 1299 days.

(21) Appl. No.: 11/499,084

(22) Filed: Aug. 3, 2006

(65) Prior Publication Data

US 2008/0051836 A1 Feb. 28, 2008

(51) Int. Cl.
*A61B 17/04* (2006.01)
(52) U.S. Cl. ...................................... 606/232
(58) Field of Classification Search ............... 606/139, 606/232, 300
See application file for complete search history.

(56) References Cited

U.S. PATENT DOCUMENTS

| 918,570 | A | 4/1909 | Mather | 292/318 |
|---|---|---|---|---|
| 919,138 | A | 4/1909 | Drake et al. | 606/144 |
| 1,153,053 | A | 9/1915 | Forster | 43/44.85 |
| 1,565,041 | A | 12/1925 | Arneu | 24/129 R |
| 2,269,963 | A | 1/1942 | Wrapler | 604/604 |
| 2,286,578 | A | 6/1942 | Sauter | 606/144 |
| 2,485,531 | A | 10/1949 | Dzus et al. | 128/92 |
| 2,600,395 | A | 6/1952 | Domoj et al. | 87/13 |
| 3,143,916 | A | 8/1964 | Rice | 85/71 |
| 3,942,407 | A | 3/1976 | Mortensen | 85/71 |
| 3,946,740 | A | 3/1976 | Bassett | 128/334 |
| 3,994,521 | A | 11/1976 | Van Gompel | 292/319 |
| 4,047,533 | A | 9/1977 | Perciaccante et al. | 128/335.5 |
| 4,109,658 | A | 8/1978 | Hughes | 128/340 |
| 4,164,225 | A | 8/1979 | Johnston et al. | 128/334 |
| 4,186,921 | A | 2/1980 | Fox | 29/461 |
| 4,210,148 | A | 7/1980 | Stivala | 606/232 |
| 4,274,324 | A | 6/1981 | Giannuzzi | 411/38 |
| 4,301,551 | A | 11/1981 | Dore et al. | 623/13.3 |
| 4,319,428 | A | 3/1982 | Fox | 47/42 |
| 4,345,601 | A | 8/1982 | Fukuda | 128/339 |
| 4,373,530 | A | 2/1983 | Kilejian | 128/334 R |
| 4,384,389 | A | 5/1983 | Sato | 24/136 K |
| 4,409,974 | A | 10/1983 | Freedland | 128/92 |
| 4,456,270 | A | 6/1984 | Zettl et al. | 279/62 |
| 4,467,478 | A | 8/1984 | Jurgutis | 606/75 |
| 4,483,023 | A | 11/1984 | Hoffman, Jr. et al. | 623/13.15 |

(Continued)

FOREIGN PATENT DOCUMENTS

DE 025 32 242 A1 2/1977

(Continued)

OTHER PUBLICATIONS

PCT International Search Report for PCT/US02/38632 2 pgs, Mailed May 16, 2003.

(Continued)

*Primary Examiner* — Melanie Tyson
*Assistant Examiner* — Son Dang
(74) *Attorney, Agent, or Firm* — Matthew Scheele; Brian Szymczak

(57) ABSTRACT

An innovative bone anchor and methods for securing soft tissue, such as tendons, to bone are described herein Such devices and methods permit a suture attachment that lies beneath the cortical bone surface and does not require tying of knots in the suture.

9 Claims, 7 Drawing Sheets

U.S. PATENT DOCUMENTS

| | | | |
|---|---|---|---|
| 4,493,323 A | 1/1985 | Albright et al. | 128/340 |
| 4,580,936 A | 4/1986 | Francis et al. | 411/38 |
| 4,590,928 A | 5/1986 | Hunt et al. | 606/72 |
| 4,597,776 A | 7/1986 | Ullman et al. | 48/197 R |
| 4,605,414 A | 8/1986 | Czajka | 623/13.11 |
| 4,621,640 A | 11/1986 | Mulhollan et al. | 128/340 |
| 4,635,637 A | 1/1987 | Schreiber | 128/337 |
| 4,657,461 A | 4/1987 | Smith | |
| 4,672,957 A | 6/1987 | Hourahane | 606/80 |
| 4,680,835 A | 7/1987 | Horng | 24/712.5 |
| 4,712,542 A | 12/1987 | Daniel et al. | 606/96 |
| 4,721,103 A | 1/1988 | Freedland | 128/92 |
| 4,731,084 A | 3/1988 | Dunn et al. | 623/13.19 |
| 4,738,255 A | 4/1988 | Goble et al. | 128/92 YF |
| 4,741,330 A | 5/1988 | Hayhurst | 123/43 R |
| 4,750,492 A | 6/1988 | Jacobs | 606/230 |
| 4,772,286 A | 9/1988 | Goble et al. | 623/13.14 |
| 4,779,616 A | 10/1988 | Johnson et al. | 606/148 |
| 4,781,182 A | 11/1988 | Purnell et al. | 128/92 |
| 4,792,336 A | 12/1988 | Hlavacek et al. | 623/13.18 |
| 4,809,408 A | 3/1989 | Abrahamson | 24/136 K |
| 4,823,780 A | 4/1989 | Odensten et al. | 606/80 |
| 4,828,439 A | 5/1989 | Giannuzzi | 411/37 |
| 4,834,755 A | 5/1989 | Silverstrini et al. | 623/13.19 |
| 4,836,205 A | 6/1989 | Barrett | 128/340 |
| 4,851,005 A | 7/1989 | Hunt et al. | 623/18 |
| 4,870,957 A | 10/1989 | Goble et al. | 606/73 |
| 4,917,700 A | 4/1990 | Aikins | 623/13.19 |
| 4,923,461 A | 5/1990 | Caspari | 606/146 |
| 4,926,860 A | 5/1990 | Stice et al. | 606/144 |
| 4,935,027 A | 6/1990 | Yoon | 606/146 |
| 4,946,467 A | 8/1990 | Ohi et al. | 606/228 |
| 4,946,468 A | 8/1990 | Li | 606/232 |
| 4,957,498 A | 9/1990 | Caspari | 606/146 |
| 4,962,929 A | 10/1990 | Melton, Jr. | 473/516 |
| 4,968,315 A | 11/1990 | Gatturna | 606/72 |
| 4,981,149 A | 1/1991 | Yoon et al. | 128/898 |
| 4,987,665 A | 1/1991 | Dumican | 28/218 |
| 5,002,550 A | 3/1991 | Li | 606/139 |
| 5,019,093 A | 5/1991 | Kaplan et al. | 606/228 |
| 5,037,422 A | 8/1991 | Hayhurst et al. | |
| 5,046,513 A | 9/1991 | Gatturna | 128/898 |
| 5,059,201 A | 10/1991 | Asnis | 606/144 |
| 5,062,344 A | 11/1991 | Gerker | 87/8 |
| 5,085,661 A | 2/1992 | Moss | 606/139 |
| 5,147,166 A | 9/1992 | Harker | |
| 5,195,542 A | 3/1993 | Gazielly et al. | 60/244 |
| 5,203,787 A | 4/1993 | Noblitt et al. | 606/232 |
| RE34,293 E | 6/1993 | Goble et al. | 623/13.14 |
| 5,217,495 A | 6/1993 | Kaplan et al. | 623/13.18 |
| 5,219,359 A | 6/1993 | McQuilkin et al. | 606/232 |
| 5,222,977 A | 6/1993 | Esser | 606/223 |
| 5,224,946 A | 7/1993 | Hayhurst et al. | |
| 5,258,016 A | 11/1993 | DiPoto et al. | 606/232 |
| 5,259,846 A | 11/1993 | Granger et al. | 606/224 |
| 5,263,984 A | 11/1993 | Li | 623/13.18 |
| 5,275,176 A | 1/1994 | Chandler | 606/242 |
| 5,304,184 A | 4/1994 | Hathaway et al. | 606/144 |
| 5,306,290 A | 4/1994 | Martins et al. | 606/232 |
| 5,312,422 A | 5/1994 | Trott | 606/144 |
| 5,318,575 A | 6/1994 | Chesterfield et al. | 606/151 |
| 5,324,308 A | 6/1994 | Pierce | |
| 5,326,205 A | 7/1994 | Anspach, III et al. | 411/43 |
| 5,330,442 A | 7/1994 | Green | 606/232 |
| 5,330,468 A | 7/1994 | Burkhart | 606/96 |
| 5,330,488 A | 7/1994 | Goldrath | 606/148 |
| 5,336,240 A | 8/1994 | Metzler | 606/232 |
| 5,354,298 A | 10/1994 | Lee et al. | |
| 5,364,407 A | 11/1994 | Poll | 606/139 |
| 5,376,118 A | 12/1994 | Kaplan et al. | 623/23.72 |
| 5,383,905 A | 1/1995 | Gold et al. | |
| 5,397,325 A | 3/1995 | Della Badia et al. | 606/144 |
| 5,405,352 A | 4/1995 | Weston | 606/148 |
| 5,405,359 A | 4/1995 | Pierce | |
| 5,409,494 A | 4/1995 | Morgan | 606/96 |
| 5,413,579 A | 5/1995 | Tom Du Toit | 606/87 |
| 5,417,691 A | 5/1995 | Hayhurst | 606/72 |
| 5,417,699 A | 5/1995 | Klein et al. | 606/139 |
| 5,417,712 A | 5/1995 | Whitaker et al. | 606/232 |
| 5,431,666 A | 7/1995 | Sauer et al. | 606/139 |
| 5,441,508 A | 8/1995 | Gazielly et al. | 606/151 |
| 5,445,167 A | 8/1995 | Yoon et al. | 128/898 |
| 5,450,860 A | 9/1995 | O'Connor | 606/224 |
| 5,454,823 A | 10/1995 | Richardson et al. | 606/148 |
| 5,464,427 A | 11/1995 | Curtis et al. | |
| 5,470,335 A | 11/1995 | Du Toit | 606/73 |
| 5,472,452 A | 12/1995 | Trott | 606/232 |
| 5,474,565 A | 12/1995 | Trott | 606/144 |
| 5,480,403 A | 1/1996 | Lee et al. | |
| 5,486,197 A | 1/1996 | Le et al. | |
| 5,499,991 A | 3/1996 | Garman et al. | 606/148 |
| 5,501,683 A | 3/1996 | Trott | |
| 5,501,695 A | 3/1996 | Anspach, Jr. et al. | 606/72 |
| 5,505,735 A | 4/1996 | Li | 606/72 |
| 5,514,159 A | 5/1996 | Matula et al. | 606/232 |
| 5,520,700 A | 5/1996 | Beyar et al. | 606/139 |
| 5,522,820 A | 6/1996 | Caspari et al. | 606/148 |
| 5,527,322 A | 6/1996 | Klein et al. | 606/144 |
| 5,527,343 A | 6/1996 | Bonutti | 606/232 |
| 5,531,792 A | 7/1996 | Huene | 623/16 |
| 5,534,012 A | 7/1996 | Bonutti | 606/232 |
| 5,540,703 A | 7/1996 | Barker, Jr. et al. | 606/139 |
| 5,545,180 A | 8/1996 | Le et al. | |
| 5,549,617 A | 8/1996 | Green et al. | 606/144 |
| 5,549,630 A | 8/1996 | Bonutti | 606/232 |
| 5,553,360 A | 9/1996 | Lucas et al. | 24/136 K |
| 5,562,689 A | 10/1996 | Green et al. | 606/151 |
| 5,569,305 A | 10/1996 | Bonutti | 606/232 |
| 5,569,306 A | 10/1996 | Thal | 606/232 |
| 5,571,104 A | 11/1996 | Li | 606/72 |
| 5,571,120 A | 11/1996 | Yoon | 606/148 |
| 5,573,540 A | 11/1996 | Yoon | 606/139 |
| 5,573,542 A | 11/1996 | Stevens | 606/144 |
| 5,573,548 A | 11/1996 | Nazre et al. | 606/232 |
| 5,575,801 A | 11/1996 | Habermeyer et al. | 606/148 |
| 5,584,835 A | 12/1996 | Greenfield | |
| 5,584,839 A | 12/1996 | Gieringer | 606/96 |
| 5,584,860 A | 12/1996 | Goble et al. | 606/232 |
| 5,584,862 A | 12/1996 | Bonutti | 606/232 |
| 5,591,207 A | 1/1997 | Coleman | 606/232 |
| 5,593,189 A | 1/1997 | Little | 289/17 |
| 5,601,558 A | 2/1997 | Torrie et al. | |
| 5,609,597 A | 3/1997 | Lehrer | 606/139 |
| 5,611,801 A | 3/1997 | Songer | 606/73 |
| 5,613,974 A | 3/1997 | Andreas et al. | 606/144 |
| 5,618,290 A | 4/1997 | Toy et al. | 606/139 |
| 5,618,314 A | 4/1997 | Harwin et al. | 606/232 |
| 5,626,614 A | 5/1997 | Hart | 606/232 |
| 5,630,824 A | 5/1997 | Hart | 606/139 |
| 5,632,748 A | 5/1997 | Beck, Jr. et al. | 606/72 |
| 5,645,552 A | 7/1997 | Sherts | 606/145 |
| 5,645,589 A | 7/1997 | Li | 623/16 |
| 5,647,874 A | 7/1997 | Hayhurst | 606/72 |
| 5,649,940 A | 7/1997 | Hart et al. | 606/148 |
| 5,658,313 A | 8/1997 | Thal | 606/232 |
| 5,665,108 A | 9/1997 | Galindo | 606/215 |
| 5,665,110 A | 9/1997 | Chervitz et al. | 606/232 |
| 5,665,112 A | 9/1997 | Thal | 606/232 |
| 5,667,528 A | 9/1997 | Colligan | 606/224 |
| D385,352 S | 10/1997 | Bales et al. | |
| 5,681,333 A | 10/1997 | Burkhart et al. | 606/148 |
| 5,681,351 A | 10/1997 | Jamiolkowski et al. | |
| 5,683,417 A | 11/1997 | Cooper | 606/223 |
| 5,683,418 A | 11/1997 | Luscombe et al. | 606/232 |
| 5,683,419 A | 11/1997 | Thal | 606/232 |
| 5,690,649 A | 11/1997 | Li | 606/139 |
| 5,693,060 A | 12/1997 | Martin | 606/148 |
| 5,697,950 A | 12/1997 | Fucci et al. | 606/232 |
| 5,702,397 A | 12/1997 | Goble et al. | |
| 5,702,398 A | 12/1997 | Tarabishy | |
| 5,707,362 A | 1/1998 | Yoon | 604/164 |
| 5,707,394 A | 1/1998 | Miller et al. | 606/232 |
| 5,709,708 A | 1/1998 | Thal | 606/232 |
| 5,720,765 A | 2/1998 | Thal | |
| 5,725,529 A | 3/1998 | Nicholson et al. | 606/72 |
| 5,725,541 A | 3/1998 | Anspach, III et al. | 606/151 |
| 5,728,136 A | 3/1998 | Thal | |

| | | | |
|---|---|---|---|
| 5,733,307 A | 3/1998 | Dinsdale | 606/232 |
| RE34,293 E | 4/1998 | Goble et al. | |
| 5,741,281 A | 4/1998 | Martin | 606/148 |
| 5,741,282 A | 4/1998 | Anspach, III et al. | 606/151 |
| 5,766,250 A | 6/1998 | Chervitz et al. | |
| 5,776,150 A | 7/1998 | Nolan et al. | 606/148 |
| 5,779,719 A | 7/1998 | Klein et al. | 606/144 |
| 5,782,863 A | 7/1998 | Bartlett | |
| 5,782,864 A | 7/1998 | Lizardi | |
| 5,782,865 A | 7/1998 | Grotz | 606/72 |
| 5,791,899 A | 8/1998 | Sachdeva | 433/173 |
| 5,792,152 A | 8/1998 | Klein et al. | 606/144 |
| 5,792,153 A | 8/1998 | Swain et al. | 606/144 |
| 5,797,927 A | 8/1998 | Yoon | 606/144 |
| 5,797,963 A | 8/1998 | McDevitt | 606/232 |
| 5,810,848 A | 9/1998 | Hayhurst | 606/144 |
| 5,810,854 A | 9/1998 | Beach | 606/232 |
| 5,814,052 A | 9/1998 | Nakao et al. | 606/148 |
| 5,814,071 A | 9/1998 | McDevitt et al. | 606/232 |
| 5,814,072 A | 9/1998 | Bonutti | 606/232 |
| 5,843,111 A | 12/1998 | Vijfvinkel | 606/171 |
| 5,849,004 A | 12/1998 | Bramlet | 606/232 |
| 5,860,978 A | 1/1999 | McDevitt | 606/72 |
| 5,860,991 A | 1/1999 | Klein et al. | 606/144 |
| 5,860,992 A | 1/1999 | Daniel et al. | 606/145 |
| 5,868,789 A | 2/1999 | Huebner | 606/232 |
| 5,879,372 A | 3/1999 | Bartlett | 606/232 |
| 5,882,340 A | 3/1999 | Yoon | 604/164 |
| 5,885,294 A | 3/1999 | Pedlick et al. | 606/80 |
| 5,891,168 A | 4/1999 | Thal | 606/232 |
| 5,893,850 A | 4/1999 | Cachia | 606/72 |
| 5,902,311 A | 5/1999 | Andreas et al. | 606/144 |
| 5,904,692 A | 5/1999 | Steckel et al. | 606/139 |
| 5,911,721 A | 6/1999 | Nicholson et al. | |
| 5,921,994 A | 7/1999 | Andreas et al. | 606/144 |
| 5,935,107 A | 8/1999 | Taylor et al. | 604/164 |
| 5,935,129 A | 8/1999 | McDevitt et al. | |
| 5,941,900 A | 8/1999 | Bonutti | 606/232 |
| 5,941,901 A | 8/1999 | Egan | 606/232 |
| 5,944,724 A | 8/1999 | Lizardi | 606/104 |
| 5,944,739 A | 8/1999 | Zlock et al. | 606/232 |
| 5,947,982 A | 9/1999 | Duran | 606/139 |
| 5,948,000 A | 9/1999 | Larsen et al. | |
| 5,948,001 A | 9/1999 | Larsen | |
| 5,948,002 A | 9/1999 | Bonutti | 606/232 |
| 5,957,953 A | 9/1999 | DiPoto et al. | 606/232 |
| 5,957,968 A | 9/1999 | Belden et al. | 607/126 |
| 5,961,530 A | 10/1999 | Moore et al. | 606/148 |
| 5,961,538 A | 10/1999 | Pedlick et al. | |
| 5,968,044 A | 10/1999 | Nicholson et al. | |
| 5,980,558 A | 11/1999 | Wiley | 606/232 |
| 5,980,559 A | 11/1999 | Bonutti | 606/232 |
| 5,984,933 A | 11/1999 | Yoon | 606/148 |
| 5,993,459 A | 11/1999 | Larsen et al. | |
| 6,001,104 A | 12/1999 | Benderev et al. | 606/80 |
| 6,001,109 A | 12/1999 | Kontos | 606/148 |
| 6,007,566 A | 12/1999 | Wenstrom, Jr. | |
| 6,007,567 A | 12/1999 | Bonutti | 606/232 |
| 6,010,525 A | 1/2000 | Bonutti et al. | 606/232 |
| 6,013,083 A | 1/2000 | Bennett | 606/104 |
| 6,017,346 A | 1/2000 | Grotz | 606/72 |
| 6,022,360 A | 2/2000 | Reimels et al. | 606/144 |
| 6,022,373 A | 2/2000 | Li | 606/232 |
| 6,024,758 A | 2/2000 | Thal | |
| 6,033,430 A | 3/2000 | Bonutti | 606/232 |
| 6,036,699 A | 3/2000 | Andreas et al. | 606/139 |
| 6,045,571 A | 4/2000 | Hill et al. | 606/228 |
| 6,045,572 A | 4/2000 | Johnson et al. | 606/232 |
| 6,045,574 A | 4/2000 | Thal | |
| 6,048,351 A | 4/2000 | Gordon et al. | 606/144 |
| 6,051,006 A | 4/2000 | Shluzas et al. | 606/148 |
| 6,053,935 A | 4/2000 | Brenneman et al. | 606/232 |
| 6,056,773 A | 5/2000 | Bonutti | |
| 6,066,146 A | 5/2000 | Carroll et al. | 606/148 |
| 6,068,648 A | 5/2000 | Cole et al. | 606/232 |
| 6,083,243 A | 7/2000 | Pokropinski et al. | 606/230 |
| 6,086,608 A | 7/2000 | Ek et al. | |
| 6,096,051 A | 8/2000 | Kortenbach et al. | 606/144 |
| 6,102,934 A | 8/2000 | Li | 606/232 |
| 6,117,160 A | 9/2000 | Bonutti | 606/215 |
| 6,117,161 A | 9/2000 | Li | 606/232 |
| 6,143,004 A | 11/2000 | Davis et al. | 606/144 |
| 6,146,386 A | 11/2000 | Blackman | 606/103 |
| 6,146,406 A | 11/2000 | Shluzas et al. | 606/232 |
| 6,149,669 A | 11/2000 | Li | 606/232 |
| 6,156,039 A | 12/2000 | Thal | 606/72 |
| 6,156,056 A | 12/2000 | Kearns et al. | 606/232 |
| 6,159,235 A | 12/2000 | Kim | |
| 6,162,537 A | 12/2000 | Martin et al. | 428/373 |
| 6,171,317 B1 | 1/2001 | Jackson et al. | 606/148 |
| 6,174,324 B1 | 1/2001 | Egan et al. | 606/232 |
| 6,200,329 B1 | 3/2001 | Fung et al. | 606/232 |
| 6,200,893 B1 | 3/2001 | Sneh | 438/685 |
| 6,206,895 B1 | 3/2001 | Levinson | |
| 6,217,592 B1 | 4/2001 | Freda et al. | 606/145 |
| 6,228,096 B1 | 5/2001 | Marchand | 606/139 |
| 6,241,736 B1 | 6/2001 | Sater et al. | 606/104 |
| 6,267,766 B1 | 7/2001 | Burkhart | 606/72 |
| 6,280,474 B1 | 8/2001 | Cassidy et al. | 623/16.11 |
| 6,293,961 B2 | 9/2001 | Schwartz et al. | 606/232 |
| 6,315,781 B1 | 11/2001 | Reinhardt et al. | |
| 6,319,252 B1 | 11/2001 | McDevitt et al. | |
| 6,319,269 B1 | 11/2001 | Li | 606/232 |
| 6,319,271 B1 | 11/2001 | Schwartz | 606/232 |
| 6,328,758 B1 | 12/2001 | Tornier et al. | 606/232 |
| 6,355,053 B1 | 3/2002 | Li | 606/232 |
| 6,409,743 B1 | 6/2002 | Fenton | 606/232 |
| 6,432,123 B2 | 8/2002 | Schwartz et al. | 606/232 |
| 6,436,109 B1 | 8/2002 | Kontos | 606/148 |
| 6,451,030 B2 | 9/2002 | Li et al. | 606/139 |
| 6,464,713 B2 | 10/2002 | Bonutti | 606/232 |
| 6,468,293 B2 | 10/2002 | Bonutti et al. | 606/232 |
| 6,471,715 B1 | 10/2002 | Weiss | 606/216 |
| 6,475,230 B1 | 11/2002 | Bonutti et al. | 606/232 |
| 6,491,714 B1 | 12/2002 | Bennett | 606/232 |
| 6,517,542 B1 | 2/2003 | Papay et al. | 606/73 |
| 6,520,980 B1 | 2/2003 | Foerster | 606/232 |
| 6,524,317 B1 | 2/2003 | Ritchart et al. | 606/72 |
| 6,527,794 B1 * | 3/2003 | McDevitt et al. | 606/232 |
| 6,540,770 B1 | 4/2003 | Tornier et al. | 606/232 |
| 6,547,800 B2 | 4/2003 | Foerster et al. | 606/151 |
| 6,551,330 B1 | 4/2003 | Bain et al. | 606/144 |
| 6,569,187 B1 | 5/2003 | Bonutti et al. | 606/232 |
| 6,575,987 B2 | 6/2003 | Gellman et al. | |
| 6,582,453 B1 | 6/2003 | Tran et al. | 606/232 |
| 6,585,730 B1 | 7/2003 | Foerster | 606/232 |
| 6,635,073 B2 | 10/2003 | Bonutti | 606/232 |
| 6,638,279 B2 | 10/2003 | Bonutti | 606/60 |
| 6,645,227 B2 | 11/2003 | Fallin et al. | 606/232 |
| 6,648,903 B1 | 11/2003 | Pierson, III | 606/232 |
| 6,652,561 B1 | 11/2003 | Tran | 606/232 |
| 6,656,183 B2 | 12/2003 | Colleran et al. | 606/232 |
| 6,660,008 B1 | 12/2003 | Foerster et al. | 606/72 |
| 6,660,023 B2 | 12/2003 | McDevitt et al. | |
| 6,679,896 B2 | 1/2004 | Gellman et al. | 606/148 |
| 6,682,549 B2 | 1/2004 | Bartlett | 606/232 |
| 6,689,154 B2 | 2/2004 | Bartlett | 606/232 |
| 6,692,516 B2 | 2/2004 | West et al. | 606/232 |
| 6,716,234 B2 | 4/2004 | Grafton | 606/228 |
| 6,736,829 B1 | 5/2004 | Li et al. | 606/232 |
| 6,770,076 B2 | 8/2004 | Foerster | 606/72 |
| 6,780,198 B1 * | 8/2004 | Gregoire et al. | 606/232 |
| 6,855,157 B2 | 2/2005 | Foerster et al. | 606/232 |
| 6,860,887 B1 | 3/2005 | Frankie | 606/104 |
| 6,939,379 B2 | 9/2005 | Sklar | 623/13.14 |
| 6,972,027 B2 | 12/2005 | Fallin et al. | 606/232 |
| 7,029,490 B2 | 4/2006 | Grafton | 606/228 |
| 7,083,638 B2 | 8/2006 | Foerster | 606/232 |
| 7,087,064 B1 | 8/2006 | Hyde | 606/142 |
| 7,090,690 B2 | 8/2006 | Foerster et al. | 606/232 |
| 7,104,999 B2 | 9/2006 | Overaker | 606/142 |
| 7,150,750 B2 | 12/2006 | Damarati | 623/17.11 |
| 7,247,164 B1 | 7/2007 | Ritchart et al. | 606/232 |
| 7,329,272 B2 | 2/2008 | Burkhart et al. | 606/232 |
| 7,527,590 B2 | 5/2009 | Suzuki et al. | 600/104 |
| 7,556,640 B2 | 7/2009 | Foerster | 606/232 |
| 7,615,061 B2 | 11/2009 | White et al. | 606/148 |
| 7,637,926 B2 | 12/2009 | Foerster et al. | 606/232 |

|  |  |  |  |  |
|---|---|---|---|---|
| 7,674,274 B2 | 3/2010 | Foerster et al. | | 606/232 |
| 7,682,374 B2 | 3/2010 | Foerster | | 606/72 |
| 7,695,494 B2 | 4/2010 | Foerster | | 606/72 |
| 7,837,710 B2* | 11/2010 | Lombardo et al. | | 606/232 |
| 7,963,972 B2 | 6/2011 | Foerster et al. | | 606/139 |
| 2001/0008971 A1 | 7/2001 | Schwartz et al. | | |
| 2003/0167062 A1 | 9/2003 | Gambale | | 606/232 |
| 2003/0195563 A1 | 10/2003 | Foerster | | 606/232 |
| 2003/0195564 A1 | 10/2003 | Tran et al. | | 606/232 |
| 2004/0093031 A1* | 5/2004 | Burkhart et al. | | 606/232 |
| 2004/0138706 A1 | 7/2004 | Abrams et al. | | 606/232 |
| 2004/0236336 A1 | 11/2004 | Foerster et al. | | 606/72 |
| 2005/0033364 A1 | 2/2005 | Gregoire et al. | | 606/232 |
| 2005/0080455 A1 | 4/2005 | Schmieding et al. | | 606/232 |
| 2005/0090827 A1 | 4/2005 | Gedebou | | 606/72 |
| 2005/0277986 A1 | 12/2005 | Foerster | | 606/232 |
| 2006/0004364 A1 | 1/2006 | Green et al. | | 606/72 |
| 2006/0074422 A1 | 4/2006 | Story et al. | | 606/142 |
| 2006/0079904 A1 | 4/2006 | Thal | | 606/72 |
| 2006/0161159 A1* | 7/2006 | Dreyfuss et al. | | 606/72 |
| 2006/0161183 A1 | 7/2006 | Sauer | | 606/142 |
| 2006/0271060 A1 | 11/2006 | Gordon | | 606/232 |
| 2006/0271105 A1 | 11/2006 | Foerster | | 606/232 |
| 2006/0276841 A1* | 12/2006 | Barbieri et al. | | 606/232 |
| 2006/0293710 A1 | 12/2006 | Foerster | | 606/72 |
| 2007/0142838 A1 | 6/2007 | Jordan | | 606/75 |
| 2008/0015594 A1 | 1/2008 | Ritchart et al. | | 606/72 |
| 2008/0319478 A1 | 12/2008 | Foerster et al. | | 606/148 |
| 2009/0069823 A1 | 3/2009 | Foerster et al. | | 606/103 |
| 2009/0222040 A1 | 9/2009 | Foerster et al. | | 606/232 |
| 2009/0222041 A1 | 9/2009 | Foerster et al. | | 606/232 |
| 2010/0191283 A1 | 7/2010 | Foerster et al. | | 606/232 |

FOREIGN PATENT DOCUMENTS

|  |  |  |
|---|---|---|
| DE | 042 35 602 A1 | 4/1994 |
| DE | 196 28 909 A1 | 1/1998 |
| EP | 0 535 906 A2 | 4/1993 |
| EP | 0 571 686 A1 | 12/1993 |
| EP | 0 611 557 A2 | 8/1994 |
| EP | 1 072 234 A2 | 1/2001 |
| EP | 1 072 237 A1 | 1/2001 |
| EP | 1987779 | 11/2008 |
| FR | 2777442 | 10/1999 |
| FR | 2777447 | 10/1999 |
| GB | 2452825 | 3/2009 |
| JP | 2286468 | 11/1990 |
| JP | 8-52154 | 2/1996 |
| JP | 08-206121 | 8/1996 |
| JP | 11-502437 | 3/1999 |
| JP | 2000-225118 | 8/2000 |
| WO | 91/06247 | 5/1991 |
| WO | 95/06439 | 3/1995 |
| WO | 95/25469 | 9/1995 |
| WO | 96/17544 | 6/1996 |
| WO | 96/28118 | 9/1996 |
| WO | 97/20522 | 6/1997 |
| WO | 98/07374 | 2/1998 |
| WO | 99/22648 | 5/1999 |
| WO | 99/53843 | 10/1999 |
| WO | 99/53844 | 10/1999 |
| WO | 02/21997 | 3/2002 |
| WO | 03/049620 | 6/2003 |
| WO | 03/090627 | 11/2003 |
| WO | 2004/082724 | 9/2004 |
| WO | 2008/022250 | 2/2008 |
| WO | 2009/032695 | 3/2009 |
| WO | 2009/114811 | 9/2009 |

OTHER PUBLICATIONS

PCT International Preliminary Examination Report for PCT/US02/38632 3pgs, Jul. 23, 2004.
European Search Report for EP02791363 4pgs, Mailed Mar. 5, 2007.
PCT Search Report and Written Opinion for PCT/US06/20657 7pgs, Mailed Oct. 2, 2007.
PCT Search Report and Written Opinion for PCT/US06/21125 6pgs, Mailed May 22, 2008.
PCT International Search Report for PCT/US01/21905 3pgs, Mailed Jan. 22, 2002.
PCT International Preliminary Examination Report for PCT/US01/21905 3pgs, Oct. 17, 2003.
PCT International Search Report for PCT/US01/17689 3pgs, Mailed Dec. 19, 2001.
PCT International Preliminary Examination Report for PCT/US01/17689 15pgs, Feb. 9, 2003.
PCT International Search Report for PCT/US02/17493 1pg, Mailed Mar. 27, 2003.
PCT International Preliminary Examination Report for PCT/US02/17493 4pgs, Sep. 8, 2003.
PCT International Search Report for PCT/US02/41018 2pgs, Mailed Jun. 5, 2003.
PCT International Preliminary Examination Report for PCT/US02/41018 3pgs, Feb. 22, 2004.
PCT International Search Report for PCT/US02/04231 1pg, Mailed Aug. 14, 2002.
PCT International Preliminary Examination Report for PCT/US02/04231 3pgs, Nov. 13, 2002.
PCT International Search Report for PCT/US03/35695 1pg, Mailed Feb. 14, 2005.
PCT International Preliminary Examination Report for PCT/US03/35695 4pgs, Dec. 21, 2005.
EP Partial European Search Report for EP02742470 3pgs, Apr. 13, 2004.
EP Supplementary European Search Report for EP02742470 5pgs, Jul. 30, 2004.
UK Search Report for GB 0816111.9 3pgs, Dec. 16, 2008.
EP Extended Search Report for EP09162639 4pgs, Oct. 28, 2009.
EP Supplementary European Search Report for EP02792506 3pgs, Mar. 24, 2010.
UK Search Report for GB 0911011.5 4pgs, Oct. 27, 2009.
UK Search Report for GB 0911013.1 4pgs, Oct. 27, 2009.
US 6,238,418, 05/2001, Schwartz et al. (withdrawn)

* cited by examiner

METHOD AND APPARATUS FOR ATTACHING CONNECTIVE TISSUES TO BONE USING A KNOTLESS SUTURE ANCHORING DEVICE

BACKGROUND OF THE INVENTION

This invention relates generally to methods and apparatus for attaching soft tissue to bone, and more particularly to anchors and methods for securing connective tissue, such as ligaments or tendons, to bone. The invention has particular application to arthroscopic surgical techniques for reattaching soft tissue in a minimally invasive procedure.

Less invasive arthroscopic techniques are beginning to be developed in an effort to address the shortcomings of open surgical repair. Working through small trocar portals allow surgeons to cause less trauma than an open procedure. However, less invasive techniques present unique challenges as the surgeon has less space to manipulate tools and implants.

Unfortunately, the skill level required to facilitate entirely arthroscopic repair tissue is inordinately high. Intracorporeal suturing is clumsy and time consuming, and only the simplest stitch patterns can be utilized. Extracorporeal knot tying is somewhat less difficult, but the tightness of the knots is difficult to judge, and the tension cannot later be adjusted. Also, because of the use of bone anchors to provide a suture fixation point in the bone, the knots that secure the soft tissues to the anchor by necessity leave the knot bundle on top of the soft tissues. In the case of certain procedures the knot bundle left in the tissue can be felt by the patient postoperatively when the patient exercises the joint. Often the knots tied arthroscopically are difficult to achieve, impossible to adjust, and are located in less than optimal areas of the shoulder. Suture tension is also impossible to measure and adjust once the knot has been fixed.

Another significant difficulty with current arthroscopic repair techniques is shortcomings related to currently available suture anchors. Suture eyelets in bone anchors available today, which like the eye of a needle are threaded with the thread or suture, are small in radius, and can cause the suture to fail at the eyelet when the anchor is placed under high tensile loads.

There are various bone anchor designs available for use by an orthopedic surgeon for attachment of soft tissues to bone. The basic commonality between the designs is that they create an attachment point in the bone for a suture that may then be passed through the soft tissues and tied, thereby immobilizing the soft tissue. This attachment point may be accomplished by different means. Screws are known for creating such attachments, but suffer from a number of disadvantages, including their tendency to loosen over time, requiring a second procedure to later remove them, and their requirement for a relatively flat attachment geometry.

Another approach is to utilize the difference in density in the cortical bone (the tough, dense outer layer of bone) and the cancellous bone (the less dense, and somewhat vascular interior of the bone). The cortical bone presents a kind of hard shell over the less dense cancellous bone. The aspect ratio of the anchor is such that it typically has a longer axis and a shorter axis and usually is pre-threaded with a suture. These designs use a hole in the cortical bone through which an anchor is inserted. The hole is drilled such that the shorter axis of the anchor will fit through the diameter of the hole, with the longer axis of the anchor being parallel to the axis of the drilled hole. After deployment in to the cancellous bone, the anchor is rotated 90 degrees so that the long axis is aligned perpendicularly to the axis of the hole. The suture is pulled, and the anchor is seated up against the inside surface of the cortical layer of bone. Due to the mismatch in the dimensions of the long axis of the anchor and the hole diameter, the anchor cannot be retracted proximally from the hole, thus providing resistance to pull-out. These anchors still suffer from the aforementioned problem of eyelet design that stresses the sutures.

Still other prior art approaches have attempted to use a "pop rivet" approach. This type of design requires a hole in the cortical bone into which a split shaft is inserted. The split shaft is hollow, and has a tapered plug leading into its inner lumen. The tapered plug is extended out through the top of the shaft, and when the plug is retracted into the inner lumen, the tapered portion causes the split shaft to be flared outwardly, ostensibly locking the device into the bone.

Other methods of securing soft tissue to bone are known in the prior art, but are not presently considered to be feasible for shoulder repair procedures, because of physicians' reluctance to leave anything but a suture in the capsule area of the shoulder. The reason for this is that staples, tacks, and the like could possibly fall out and cause injury during movement. As a result of this constraint, the attachment point often must be located at a less than ideal position. Also, the tacks or staples require a substantial hole in the soft tissue, and make it difficult for the surgeon to precisely locate the soft tissue relative to the bone.

As previously discussed, any of the anchor points for sutures mentioned above require that a length of suture be passed through an eyelet fashioned in the anchor and then looped through the soft tissues and tied down to complete the securement. Much skill is required, however, to both place the sutures in the soft tissues, and to tie knots while working through a trocar under endoscopic visualization.

There have been attempts to solve some of the problems that exist in current anchor designs. One such approach is disclosed in U.S. Pat. No. 5,324,308 to Pierce. In this patent, there is disclosed a suture anchor that incorporates a proximal and distal wedge component having inclined mating faces. The distal wedge component has two suture thread holes at its base through which a length of suture may be threaded. The assembly may be placed in a drilled hole in the bone, and when tension is placed on the suture, the distal wedge block is caused to ride up against the proximal wedge block, expanding the projected area within the drilled hole, and locking the anchor into the bone. This approach is a useful method for creating an anchor point for the suture, but does not in any way address the problem of tying knots in the suture to fix the soft tissue to the bone.

The problem of placing sutures in soft tissues and tying knots in an endoscopic environment is well known, and there have been attempts to address the problem and to simplify the process of suture fixation. One such approach is disclosed in U.S. Pat. No. 5,383,905 to Golds et al. The patent describes a device for securing a suture loop about bodily tissue that includes a bead member having a longitudinal bore and an anchor member adapted to be slidably inserted within the bore of the bead member. The anchor member includes at least two axial compressible sections which define a passageway to receive two end portions of a suture loop. The axial sections collapse radially inwardly upon insertion of the anchor member within the bore of the bead member to securely wedge the suture end portions received within the passageway.

Although the Golds et al. patent approach utilizes a wedge-shaped member to lock the sutures in place, the suture legs are passing through the bore of the bead only one time, in a proximal to distal direction, and are locked by the collapsing of the wedge, which creates an interference on the longitudinal bore of the anchor member. Also, no provision is made in this design for attachment of sutures to bone. The design is primarily suited for locking a suture loop, such as is used for ligation or approximation of soft tissues.

An approach that includes bone attachment is described in U.S. Pat. No. 5,584,835 to Greenfield. In this patent, a two part device for attaching soft tissue to bone is shown. A bone anchor portion is screwed into a hole in the bone, and is disposed to accept a plug that has been adapted to receive sutures. In one embodiment, the suture plug is configured so that when it is forced into its receptacle in the bone anchor portion, sutures that have been passed through an eyelet in the plug are trapped by friction between the wall of the anchor portion and the body of the plug portion.

Although there is some merit to this approach for eliminating the need for knots in the attachment of sutures to bone, a problem with being able to properly set the tension in the sutures exists. The user is required to pull on the sutures until appropriate tension is achieved, and then to set the plug portion into the bone anchor portion. This action increases the tension in the sutures, and may garrote the soft tissues or increase the tension in the sutures beyond the tensile strength of the material, breaking the sutures. In addition, the minimal surface area provided by this anchor design for pinching or locking the sutures in place will abrade or damage the suture such that the suture's ability to resist load will be greatly compromised.

A disclosure that incorporates bone attachment and eliminates knot tying is set forth in U.S. Pat. No. 5,702,397 to Goble et al. One embodiment, in particular, is shown in FIG. 23 of that patent and includes a bone anchor that has a threaded body with an inner cavity. The cavity is open to one end of the threaded body, and joins two lumens that run out to the other end of the threaded body. Within the cavity is disposed a gear, journaled on an axle. A length of suture is threaded through one lumen, around the gear, and out through the other lumen. A ball is disposed within the cavity to ride against a tapered race and ostensibly lock the suture in place. What is not clear from the patent disclosure is how the force D shown as the tension in the suture would lock the ball into the race. Although this embodiment purports to be a self-locking anchor adapted for use in blind holes for fixing sutures into bone, the construct shown is complicated, and does not appear to be adequate to reliably fixate the suture.

PCT Publication WO 01/10312 to McDevitt et al. also describes a self-locking suture anchor for attaching soft tissue to bone. In this device a tissue anchor holds a filament within the anchor so that an applied force greater than a threshold force causes the filament to move longitudinally, while an applied force that is less than the threshold force does not move the filament.

In view of the above, what is needed, is a new approach for repairing or fixing other soft tissues to bone, wherein suture tension can be adjusted and possibly measured, the suture anchor resides below the cortical bone surface, there is no requirement for the surgeon to tie a knot to attach the suture to the bone anchor, and wherein the procedure associated with the new approach is better for the patient, saves time, is uncomplicated to use, and easily taught to practitioners having skill in the art.

SUMMARY OF THE INVENTION

The present invention solves the problems outlined above by providing innovative bone anchor and connective techniques which permit a suture attachment that lies beneath the cortical bone surface. The present invention discloses devices and methods for securing sutures to a bone anchor without the requirement of knot tying.

One variation of the system includes a knotless suture anchoring system for anchoring a length of suture with respect to a body cavity, comprising, an anchor body having at least one anchoring structure allowing for securing the anchor body within the body cavity, the anchor body having a proximal end, a distal end, and a lumen extending therebetween, a locking plug slidably coupled to the distal end of the anchor body and having a distal stop and a shaft portion, the distal stop being sized to prevent entry into the anchor body lumen, where the shaft portion is sized relative to the anchor body lumen to allow movement therein when no suture is located within the anchor body lumen and a friction fit when the suture is located in the anchor body lumen, a suture carrying portion in the distal stop allowing the suture to pass from a first side of the locking plug to an opposite side of the locking plug; and a snare extending through anchor body lumen and the suture carrying portion such that when the distal portion of the snare is affixed to the suture, withdrawal of the snare pulls the suture through the suture carrying portion and the anchor body lumen.

Another variation of the system includes a knotless suture anchoring system, comprising a suture having a tissue engaging portion, an anchoring portion and a mid portion therebetween, an anchor body having at least one rigid anchoring structure allowing for securing the anchor body within the body cavity, the anchor body having a proximal end, a distal end, and a lumen extending therebetween, a locking plug having a distal stop and a shaft portion at least partially located within the anchor body lumen, the distal stop being sized to prevent entry into the anchor body lumen, where the shaft portion is under sized relative to the anchor body lumen, a suture carrying portion in the distal stop allowing the suture to pass from a first side of the locking plug to an opposite side of the locking plug, and where the tissue engaging portion extends externally to the anchor body, the anchoring portion extends within the anchor body lumen, and where the mid portion extends in the suture carrying portion.

The present invention also includes methods of securing soft tissue with respect to a body cavity without knots. In one variation such a method comprises passing a length of suture through soft tissue so that a portion of the suture is secured in the soft tissue resulting in at least one free end, providing an anchor comprising an anchor body having a lumen extending therethrough, and a locking plug having a shaft portion extending at least partially in the anchor body lumen, passing the free end of the suture into the anchor such that a first section of the suture is in a portion of the locking plug and extends through the anchor body lumen, applying tension to the suture between the tissue and the anchor, and inserting the anchor into the body cavity, such that a second section of the suture is between the anchor body and a wall of the body cavity.

Another variation of a method includes providing an anchor having an anchor body and a locking plug, where the locking plug is moveable through a lumen of the anchor body until a stop of the locking plug contacts the anchor body, securing a suture to the soft tissue, advancing a first section of the suture through the stop and through the body lumen, tensioning a portion of the suture, and securing the anchor into a cavity formed in the hard tissue, such that the first section of the suture is compressed between the anchor body and the locking plug and a second section of the suture is compressed between a wall of the cavity and an exterior of the anchor body.

As discussed herein, the anchors and deployment system may be used in any part of the body but has particular applications in attaching the glenoid labrum to the glenoid.

Now, it is to be understood that the above described invention is particularly suited to locking sutures that have been passed through soft tissues and are to be anchored to bone. The creation of an anchor point within the bone is discussed in U.S. patent application Ser. No. 09/616,802, entitled *Method & Apparatus for Attaching Connective Tissues to Bone Using a Suture Anchoring Device*, filed on Jul. 14, 2000. The referenced application is commonly assigned with the present application, and is incorporated by reference in its entirety herein. Other prior art anchors, such as screws, moly bolts, and pop rivets may be adapted for use with the present invention as well.

The invention, together with additional features and advantages thereof, may best be understood by reference to the following description taken in conjunction with the accompanying illustrative drawing.

DESCRIPTION OF THE PREFERRED EMBODIMENT

The present invention provides improved methods and devices for knotless suturing of tissue. Although the variation discussed herein discusses use of a suture, the term "suture" may include any piece of material that is used to close a wound or connect tissue (e.g., catgut, thread, wire, etc.) so long as the material can be used with the other portions of the anchor as described herein. Accordingly, sutures as described herein may include polymeric, metallic, or other types of sutures.

For illustrative purposes, the examples discussed herein show the use of the anchoring system to suture soft tissue to a bone structure, specifically the soft labrum to the glenoid. In one variation of the system, the medical practitioner affixes a length of suture through soft tissue to approximate and fix the soft tissue with respect to the body cavity (e.g., a bored hole in the bone structure). It should be understood, however, that the suture anchor apparatus may be utilized to secure a length of suture to body cavities other than in a bone structure, and may even be used to anchor the suture outside of a body cavity, merely to a predetermined location within the body.

In the suturing system described herein, the medical practitioner affixes the suture to an anchor body that is placed in the body cavity. The design of the system eliminates the needs for knotting of the suture. However, the present system also allows tying of an end of the suture into a knot if the practitioner so desires.

The invention permits minimally invasive surgeries on injuries and greatly facilitates rapid and secure fixation of the target tissues. It should be understood that the same principles described herein apply to the repair of other injuries in which soft tissue is to be re-attached to a bone structure.

Figure 1A:
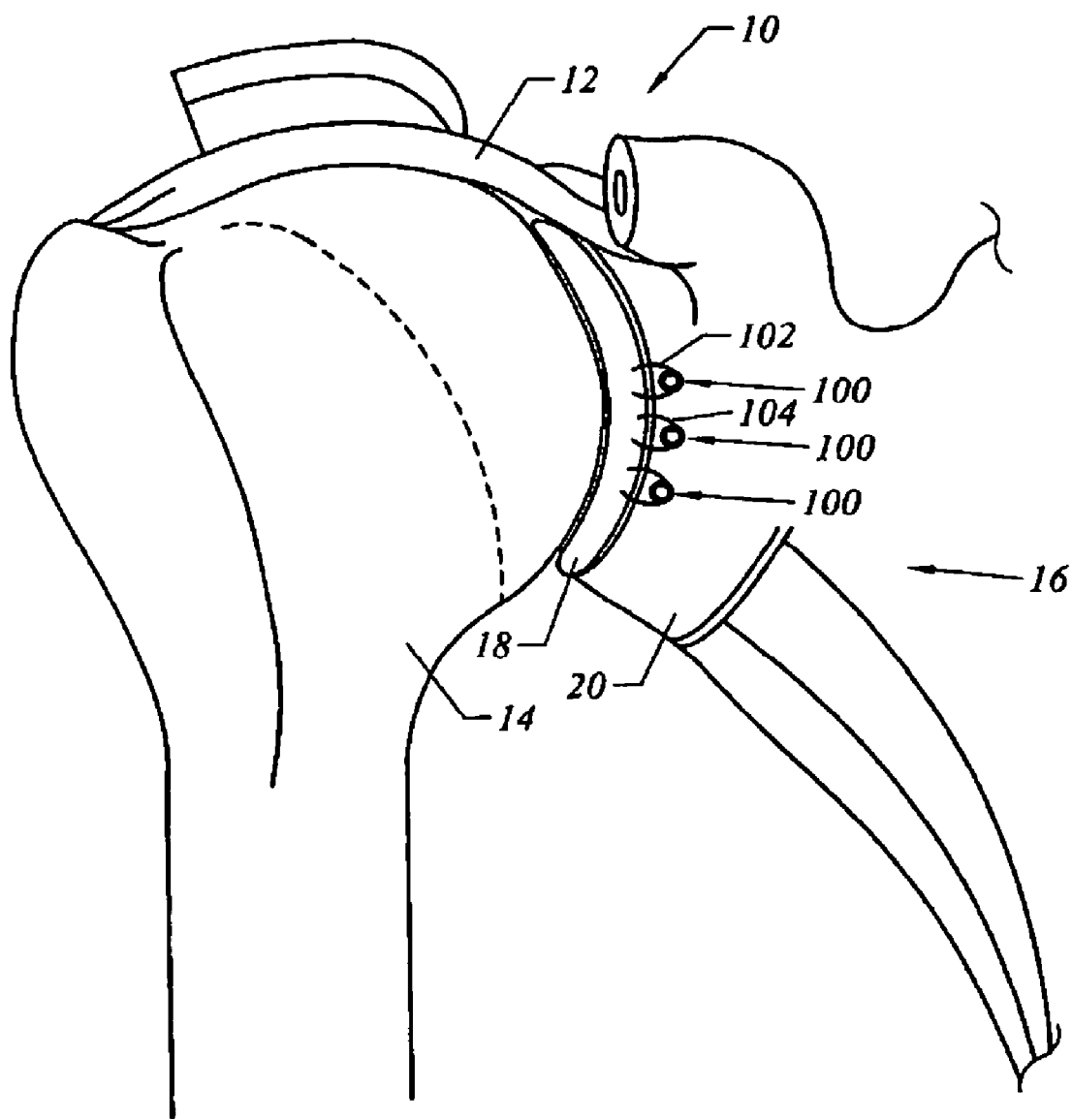
FIG. 1A illustrates a partial view of the shoulder anatomy in which the humerus is adjacent to the rotator cuff and labrum as it nests within against the glenoid and anchors placed in the labrum in accordance with the invention.

FIG. 1A illustrates a partial view of the shoulder anatomy 10 in which the humerus 14 is adjacent to the rotator cuff 12 and labrum 18 as it nests within against the glenoid 20. The scapula 16 is partially shown. For clarity, various bones and other soft tissue are not illustrated in FIG. 1A.

FIG. 1A also illustrates exemplary placement of anchors 100 according to the system described herein. As shown, the anchor 100 secures soft tissue (e.g., the labrum) to hard tissue (e.g., the glenoid) via a suture 102. Any number of anchors 100 may be employed. Moreover, the location of the anchors and sutures may vary as required. As shown, the anchor body 104 is located within a cavity in the bone. This cavity is created prior to affixing the anchor within the bone.

Figure 1B:
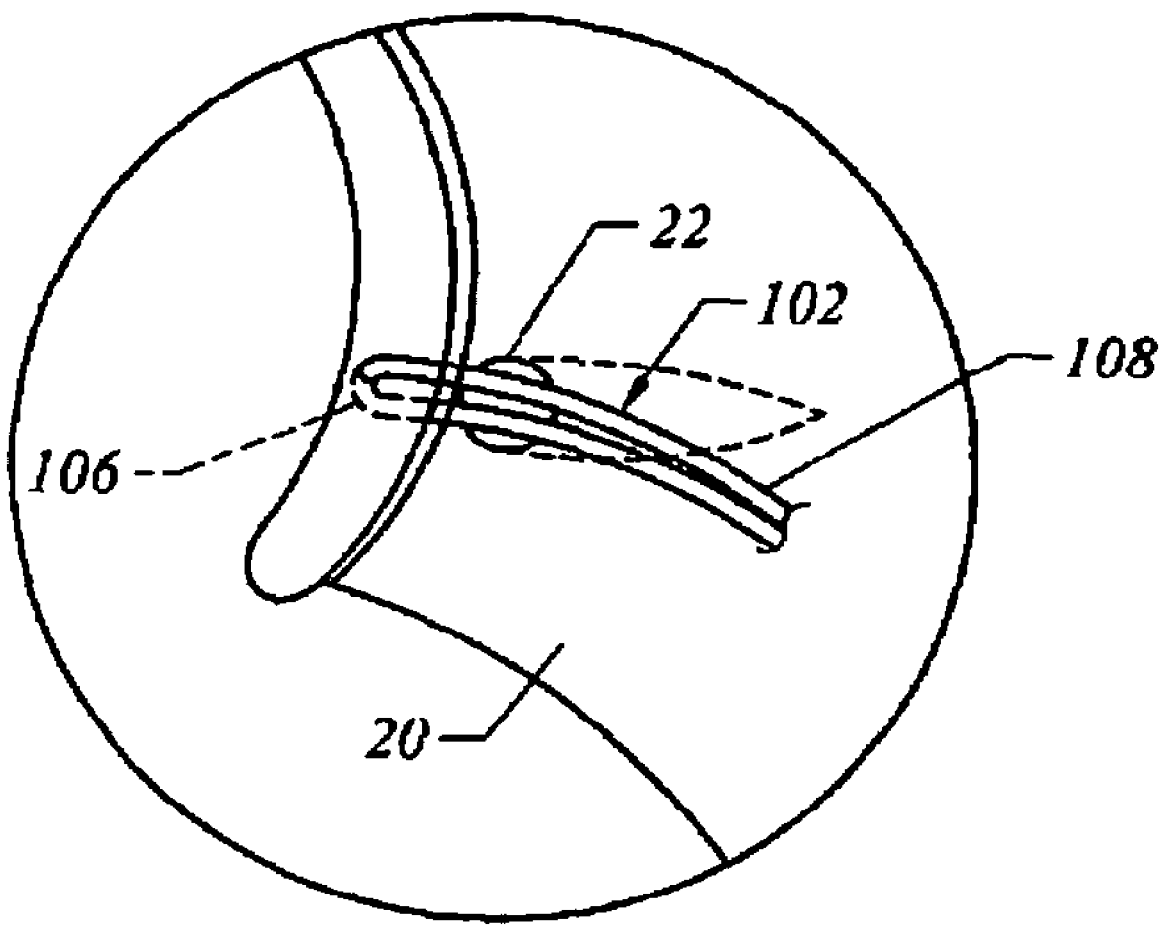
FIG. 1B is another view of a suture within the labrum and adjacent to a cavity created in the bone but where the suture is yet to be coupled to an anchor.

FIG. 1B shows a view of a single suture 102 adjacent to a cavity 22 created in the bone. At this point, the free ends 108 of the suture 102 do not enter the cavity but are directed towards the anchoring system (not shown) as described in further detail below. FIG. 1B illustrates placement of the suture 102 within the labrum 18. In this example, a looping 106 section secures the suture 102 to the labrum 18. The looping section 106 may extend through the tissue so that both free ends 108 of the suture 102 can be loaded into the anchor (not illustrated in FIG. 1B).

Typically, the soft tissue is grasped or stabilized using a device while needles place a stitch in the tissue. An example of a device capable of placing the suture is the SPEED STITCH™ Suturing device provided by ArthroCare, Sunnyvale Calif. However, the methods and devices described herein are not limited to such a technique. For example, a single end of the suture may be affixed to soft tissue such that the other free end of the suture is eventually affixed to the bone via the anchor.

The hole or cavity 22 sites are planned by applying traction to the suture. This action allows the practitioner to estimate the proximity of the holes to the labrum. Typically, the holes 22 are created 2 mm from the glenoid rim onto the articular surface of the glenoid. However, in certain cases, the holes 22 may be created on the glenoid rim.

Figure 2A:
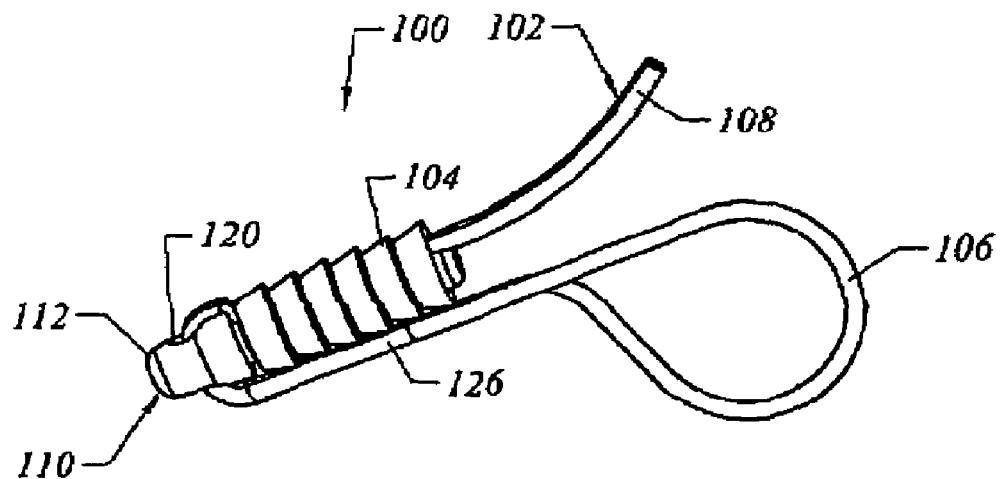
FIG. 2A shows a view of the anchor and suture in a deployed configuration.
Figure 2B:
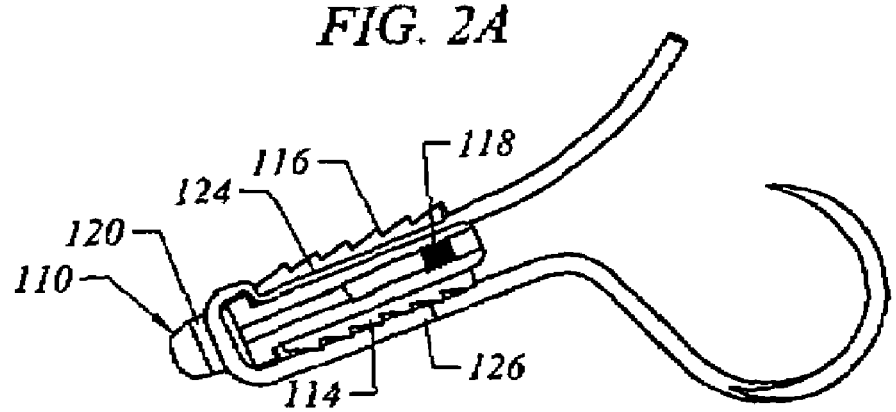
FIG. 2B shows a cross sectional view of the anchor as it compresses a section of the suture within the anchor.

FIG. 2A illustrates an example of a deployed anchor 100 having a suture 102. As shown, the anchor 100 includes an anchor body 104 that seats a locking plug 110. FIG. 2B shows a cross-sectional view of the anchor 100 of FIG. 2A. As discussed herein, a first section 124 of the suture 102 becomes secured within the anchor 100 while a second section 126 wedges between the cavity wall (not shown) and an exterior of the anchor body 104. In this variation, the suture 102 loops from a first side of the anchor to a second side via a suture opening 120 located in a stop portion 112 of the locking plug 110.

Figure 2C:
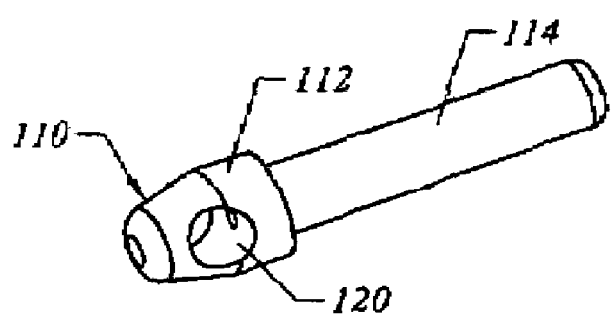
FIGS. 2C and 2D show a variation of anchor components.

FIG. 2C illustrates an example of a locking plug 110. The locking plug 110 includes a shaft 114 intended to nest within the anchor body. The locking plug 110 also includes a stop portion 112 that limits movement of the plug 110 within the anchor body. Although the shaft portion 114 is illustrated as being smooth and cylindrical, the devices described herein include various additional combinations of shapes and textures or surfaces on the shaft. In particular, the surface of the shaft 114 may be configured to increase the frictional force applied by the anchor against the suture portion held therein. In addition, the suture opening 120 is illustrated as an opening within the stop portion 112. However, other shapes and locations of the suture holder 120 may be incorporated into the anchor. For example, the suture opening 120 may not be fully surrounded by the stop portion 112 (e.g., a groove in the face of the stop portion). Alternatively or in combination, the suture opening 120 may be located in the shaft portion 114 of the locking plug 110.

Turning back to FIG. 2B, the shaft 114 of the locking plug 110 may include a section allowing for a removable connection with the anchor system 150. In this variation, the removable connection comprises an internal threaded portion 118 within the shaft. As discussed herein, in one variation, upon application of sufficient stress between the mating threaded portions, one or both of the threaded portions strip to allow for a release of the anchor 100 from the system 150. In additional variations, other removable connections as commonly known by those skilled in the art are contemplated to be within the scope of the invention.

Figure 2D:
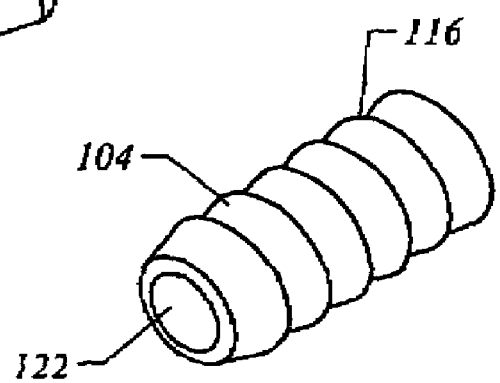

FIG. 2D illustrates an example of an anchor body 104. As shown, the anchor body includes a lumen 122 that is sufficiently sized to permit passage of the locking plug shaft 114. In addition, this variation of the anchor body 114 is non-deformable or rigid and includes a plurality of tapered ridges 116 or anchoring structures that deform the tissue upon placement of the anchor into the body cavity. As shown, the tapering shape of the ridges 116 allow for insertion of the anchor body into the cavity when inserted in a first direction and resist removal when the anchor body is urged in an opposite direction. The illustration of the ridges 116 is intended for example only. Variations are within the scope of the device and methods described herein. For example, variations include anchoring structures that do not fully encircle the anchor body. In additional versions of the device, the anchor body may be slightly deformable such that it at least partially conforms to the body cavity.

Figure 3A:
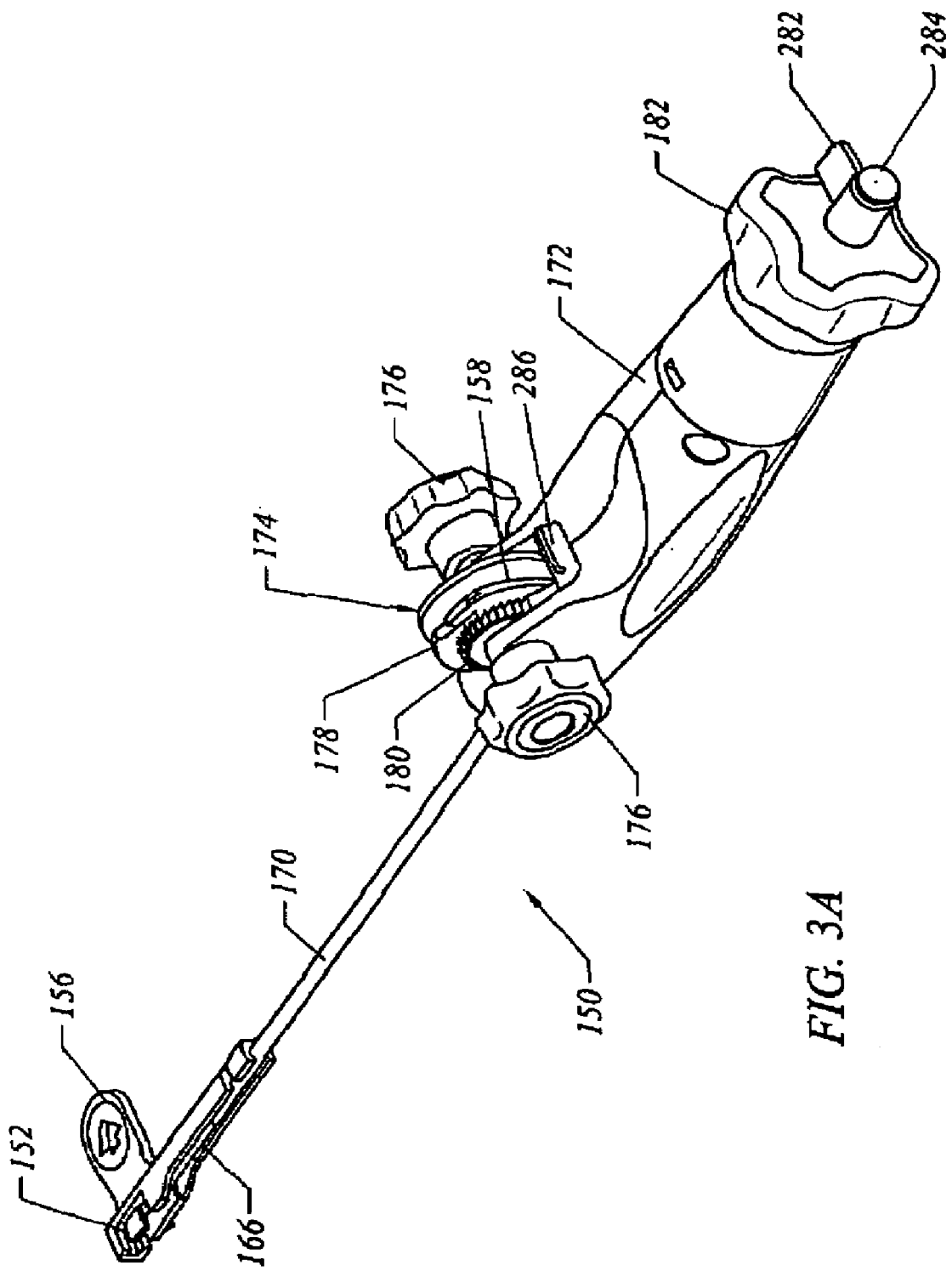
FIG. 3A illustrates a perspective view of a variation of an anchoring system as described herein.

FIG. 3A illustrates a variation of the suture anchoring system 150 as described with an anchor located in the distal portion of the system 150. As shown, a snare 152 is placed within the anchor to allow the medical practitioner to load a suture for securing tissue. A removable snare body holder 156 can be used to prevent the snare 152 from becoming damaged or from disengaging the anchor during, for example, handling and shipment. The system 150 includes an extension member 170 extending from a handle portion 172. The distal end of the extension member 170 includes an anchor seat 166 while a rod (not shown) is located within the extension member 170. In use, the rod is moveable relative to the anchor seat 166 to assist in deploying or disengaging the anchor from the system 150.

In the embodiment shown in FIG. 3A, the handle portion 172 includes a wheel or spool member 174. The spool member may have one or more knobs 176 associated with it that allow for tensioning of the suture for tissue approximation. In this particular variation, a spool 178 allows for retraction of the snare 158. As the wheel is rotated, the snare and suture may be drawn through the system 150. The spool member 174 may also include a locking mechanism 180 (such as the locking ratchet configuration shown) to prevent undesired movement (e.g., back out) of the suture and/or snare. The handle portion 172 may also include a lever 182 that moves the inner rod relative to the extension member 170 and anchor seat 166. In this variation the lever 182 comprises a rotational lever or cam. As discussed below, using the lever to advance an anchor body against a stop portion on the locking plug ultimately disengages the anchor from the system 150.

Figure 3B:
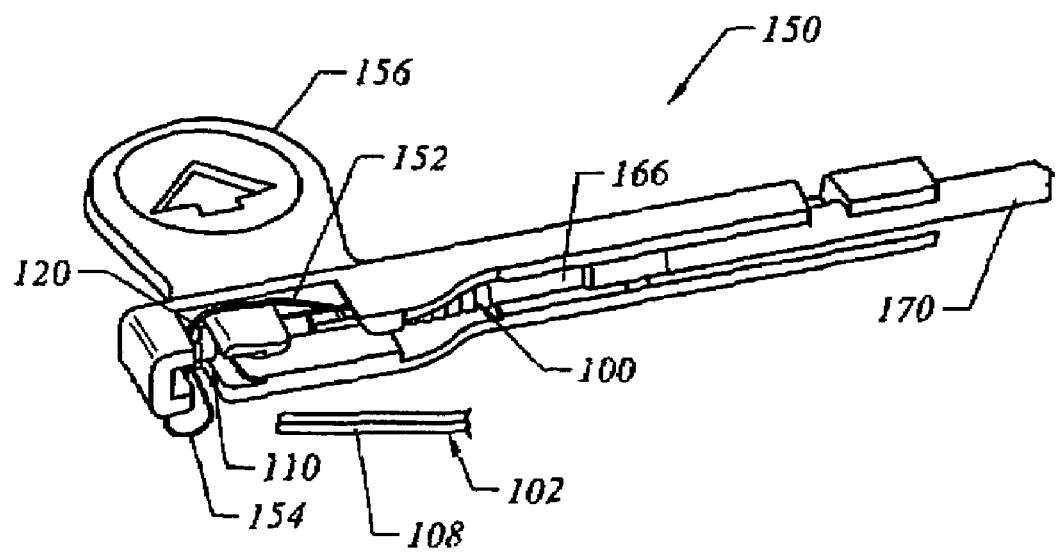
FIGS. 3B and 3C show a distal end of the anchoring system with a snare and suture respectively.

FIG. 3B illustrates a distal end of the suture anchoring system 150 according to the present devices and methods. To load the suture 102 in the anchoring system 150, the medical practitioner passes the free end or ends 108 of the suture 102 into a snare 152. The snare 152 extends through the anchor 100 and anchoring system and can be coupled to the spool member (not shown). In the variation shown, the snare 152 comprises a wire terminating in a loop 154 as shown. Alternatively, the snare 152 may have any other means of permanently or temporarily securing the suture 102 so that it may be passed into the anchoring system (e.g., clamps, hooks, sleeves, etc.). Moreover, it is not necessary to capture the ends of the suture 102. Instead, the practitioner may extend the suture beyond the loop.

Figure 3C:
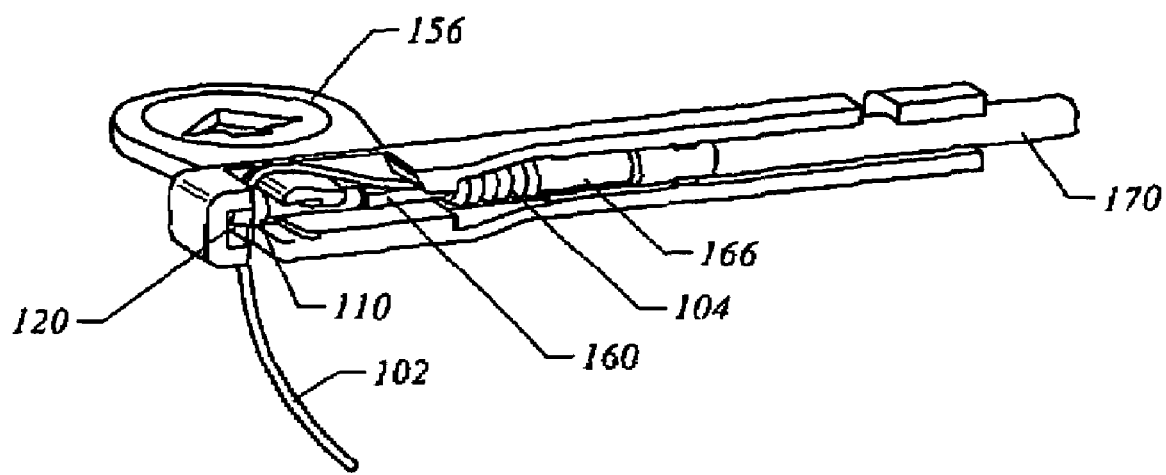

Next, the medical practitioner draws the suture 102 through the anchor 100 and into the anchoring system 150 (for example, via activation of the spool member). The result is shown in FIG. 3C, which shows the suture 102 extending through a portion 112 of a locking plug 110 to pass from a first side of the anchor 100 to an adjacent side through the suture carrying portion 120 of the locking plug 110. Ultimately, the suture 102 passes through the anchor body 104. This configuration allows loading of the suture 102 into the interior lumen of the anchor body 104. Although not illustrated, the suture 102 can be withdrawn into a handle portion of the device for tensioning prior to placement.

Figure 4A:
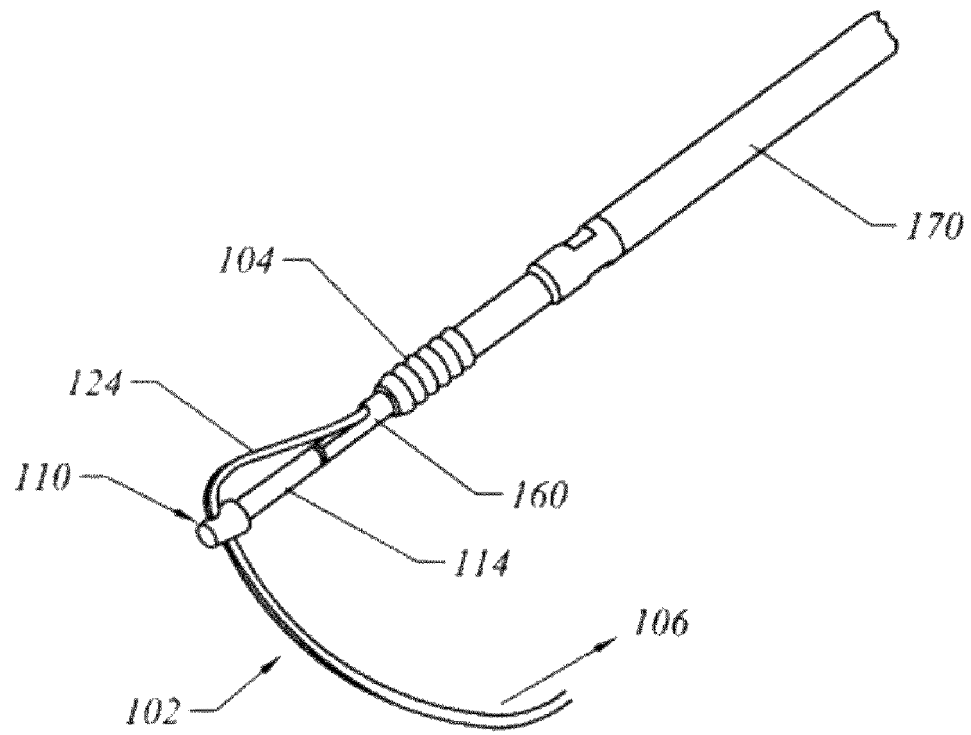
FIGS. 4A-4B show a perspective view and cross sectional view respectively prior to compressing a suture within the anchor.

FIG. 4A illustrates the assembly after the medical practitioner removes the snare body holder 156 so that the assembly is ready for insertion into a body cavity 22. At this point, the medical practitioner can adjust the tension in the suture 102 by adjusting the suture 102 length between the section of the suture that is placed in tissue (not shown but designated by 106) and the locking plug 110. As described herein, the adjustment may be performed using the spool assembly or a similar tensioning system. As discussed herein, a first section 124 of the suture 102 is situated so that it remains inside the deployed anchor 100.

Figure 4B:
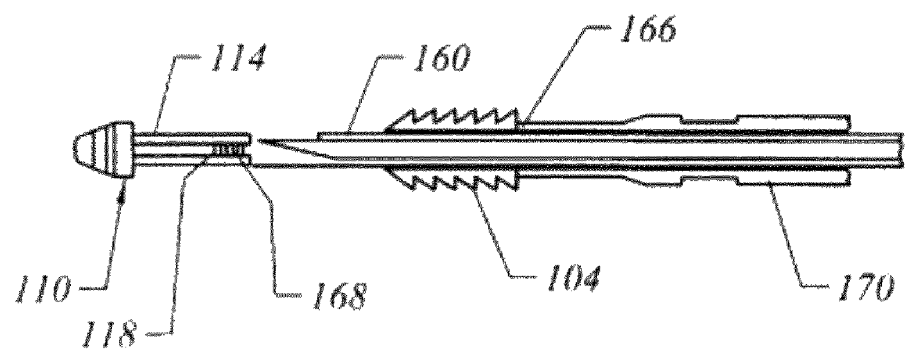

FIG. 4B illustrates a cross sectional view of the device of FIG. 4A. In this view the suture is omitted for clarity. As illustrated, the shaft 114 of the locking plug 110 includes a threaded portion 118 that receives a threaded rod portion 168. As noted herein, the devices and methods include various configurations for removably connecting the shaft 114 to the rod 160 other than threading. For example, a frictional press-fit or barbed coupling may be employed.

Figure 4C:
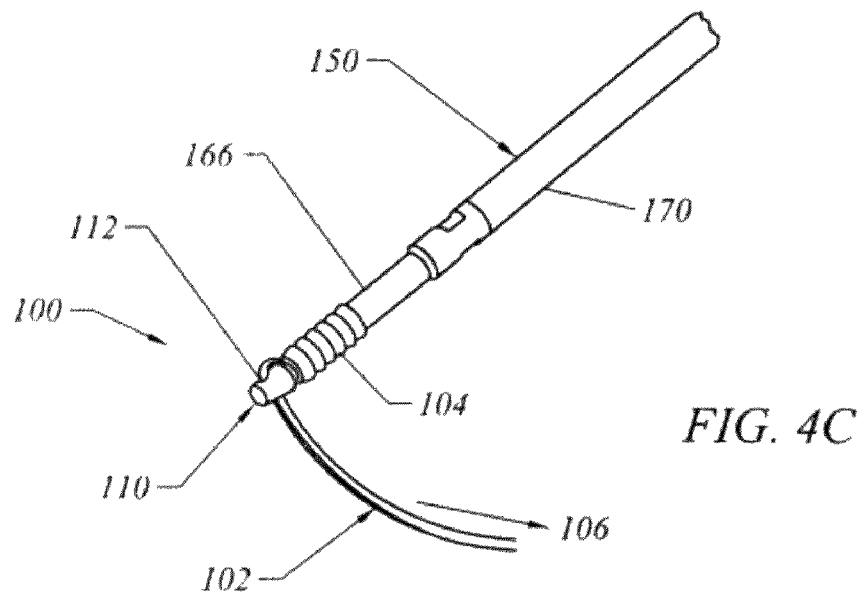
FIGS. 4C-4D show a perspective view and cross sectional view respectively after the components of the anchor are joined to retain a suture therein.

FIG. 4C illustrates the anchor 100 upon deployment but before it is disengaged from the system 150 and anchor seat 166. As shown, the anchor body 104 slides over the shaft 114 of the locking plug 110 to trap the first section (not shown) of the suture 102 within the anchor body 104. In some variations, the first section 124 of the suture 102 may be withdrawn into the system 150 as the anchor body 104 advances onto the shaft 114 of the plug 110. Ultimately, the stop portion 112 of the locking plug 110 contacts the anchor body 104.

In this variation of the invention, the body is urged over the shaft of the plug by first, rotating ninety (90) degrees a flag 282 and button 284. The button 284 and flag 282 are used to lockout (prevent relative movement between the anchor and plug) during the initial placement of the anchor into the bone passage. Next, the surgeon pushes or taps on the button 284 which drives body 104 onto plug 110. While the anchor body is being urged onto the plug, internal ratchet teeth ensure that the members 140/166/170 can not back out between taps. When the button 284 is flush with the back of member 182, body 104 is pushed all the way onto the shaft 114 and the suture is locked.

In one embodiment of the invention, the operator may further tension the suture (approximate tissue) by urging or pounding the anchor into the hole by continuing to tap on the button. This action will serve to urge the anchor, with suture attached, deeper into the hole thus dragging the tissue.

Figure 4D:
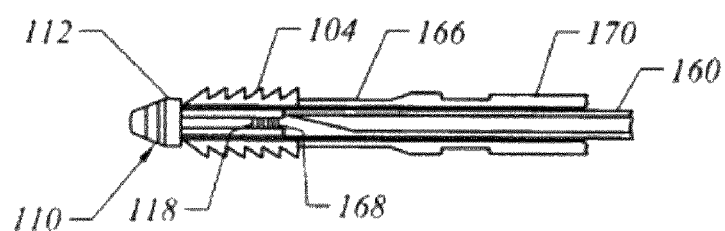

Referring again to FIGS. 3A and 4D to separate the anchor from anchor seat 166, the rotating lever knob 182 is twisted to push seat 166 further into plug 110 which ultimately strips the threaded rod portion 168 out of member 118. A driver block (not shown) simultaneously releases the suture ratchet reel 174 so the suture can pay out as the inserter is being removed. This is accomplished by the driver block actuating a stop 286 proximal to spool 174.

Figure 4E:
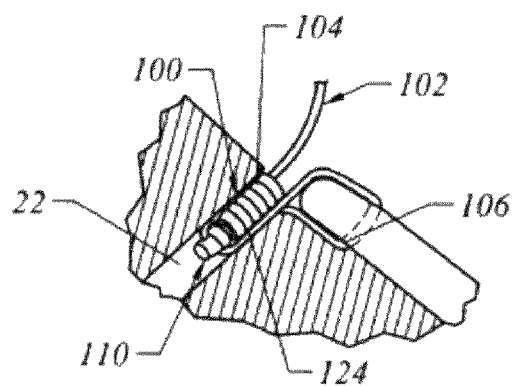
FIG. 4E shows a partial sectional view of an anchor placed within a cavity and attached to soft tissue.

FIG. 4E shows a deployed anchor 100 situated within the body cavity 22 after release from the anchoring system 150. As shown, the anchor body 104 compresses a second section 124 of the suture 102 against a wall of the cavity 22. The first section of the suture 102 remains within the anchor between the locking plug 110 and interior of the anchor body 104.

Although the variation depicts the portion of the anchor as being adjacent to the surface of the hard tissue, variations of the method and device include anchors that are deployed partially above or fully below the surface of the tissue. As shown, the anchor body 104 impinges a second section 124 of the suture against a wall of the cavity 22. Accordingly, the act of inserting the anchor body 104 into the cavity 22 actually increases the tension on the soft tissue since the anchor body 104 further drives the second suture section 124 into the cavity 22 during placement.

Another variation of a method for deploying the anchor includes advancing the anchor body 104 over the shaft 114 when the assembly is located within the cavity. For example, the locking plug 110 may be inserted into the cavity prior to advancement of the anchor body 104 onto the shaft 114 (as shown by the configuration of FIG. 4A). Next, the medical practitioner can adjust the tension on the suture 102 until a desired length of suture extends from the cavity to the soft tissue. Finally, the medical practitioner advances the anchor body 104 into the cavity. At the same time, the anchor advances over the locking plug shaft 114. This action produces the configuration shown in FIG. 4C. Again, the action of the anchor body 104 serves to further secure the soft tissue as the anchor body 104 drives the second section 124 of the suture 102 further into the cavity and ultimately deploys the anchor as shown in FIG. 4E.

The amount of force required to separate the anchor from the deployment system is sufficiently high to minimize inadvertent deployment but also to ensure that the surgeon can deploy the anchor as desired.

One advantage provided by the present invention is the ability to tighten a suture loop embedded within soft tissue to a predetermined tension, and lock the suture within a suture anchor without losing that tension.

Accordingly, although an exemplary embodiment of the invention has been shown and described, it is to be understood that all the terms used herein are descriptive rather than limiting, and that many changes, modifications, and substitutions may be made by one having ordinary skill in the art without departing from the spirit and scope of the invention. In particular, it is noted that the procedures, while oriented toward the arthroscopic repair of the rotator cuff, are applicable to the repair of any body location wherein it is desired to attach or reattach soft tissue to bone, particularly using an arthroscopic procedure.

What is claimed is:

1. A knotless suture anchoring system, comprising:
   a suture having a tissue engaging portion, an anchoring portion and a mid portion therebetween;
   an anchor body having at least one rigid anchoring structure allowing for securing the anchor body within the body cavity, the anchor body having a proximal end, a distal end, and a lumen extending therebetween;
   a locking plug having a distal stop and a shaft portion at least partially located within the anchor body lumen, the distal stop being sized to prevent entry into the anchor body lumen, where the shaft portion is under sized relative to the anchor body lumen such that insertion of the shaft into the lumen does not deform the anchor body;
   a suture carrying portion associated with one of the distal stop or shaft portion allowing the suture to pass from a first side of the locking plug to an opposite side of the locking plug;
   where the tissue engaging portion extends from the distal end to the proximal end of the body exterior and is wedged between the body cavity and exterior of body anchor, the anchoring portion extends within the anchor body lumen, and where the mid portion extends in the suture carrying portion.

2. The system of claim 1, where the anchor body is generally tubular and has a plurality of ridges circumferentially located about the anchor body.

3. The system of claim 2, where the ridges are tapered to permit insertion of the anchor body into the body cavity when advanced in a first direction and resist removal of the anchor body when withdrawn in an opposite direction.

4. The system of claim 1, where the locking plug shaft is smooth.

5. The system of claim 1, wherein the anchoring portion is secured within the anchor body.

6. The system of claim 1, wherein the locking plug is slidably movable within the anchor body lumen.

7. The system of claim 1, wherein the locking plug comprises an internal threaded portion operable for removable connection with a rod.

8. The system of claim 7, wherein the rod is adapted for coupling to an actuation assembly having a handle portion and where the actuation assembly further comprises a spool member operable to engage the suture, such that actuation of the spool member allows for tensioning of the suture.

9. The system of claim 7, further including a section of tensile weakness along the rod permitting the rod to be detached from the shaft upon application of a predetermined tensile force on the rod in the proximal direction after the distal stop contacts the anchor body.

* * * * *